(12) United States Patent
Phelps

(10) Patent No.: US 11,877,777 B2
(45) Date of Patent: Jan. 23, 2024

(54) ARTIFICIAL SPINAL DISK PROSTHESIS

(71) Applicant: GLOBUS MEDICAL, INC., Audubon, PA (US)

(72) Inventor: Jeff Phelps, North Richland Hills, TX (US)

(73) Assignee: Globus Medical, Inc, Audubon, PA (US)

( * ) Notice: Subject to any disclaimer, the term of this patent is extended or adjusted under 35 U.S.C. 154(b) by 0 days.

(21) Appl. No.: 17/824,105

(22) Filed: May 25, 2022

(65) Prior Publication Data

US 2022/0280204 A1  Sep. 8, 2022

Related U.S. Application Data

(63) Continuation of application No. 16/865,510, filed on May 4, 2020, now Pat. No. 11,369,420, which is a continuation of application No. 16/046,000, filed on Jul. 26, 2018, now Pat. No. 10,716,599, which is a continuation of application No. 15/367,456, filed on Dec. 2, 2016, now Pat. No. 10,034,763, which is a
(Continued)

(51) Int. Cl.
| | |
|---|---|
| *A61B 17/70* | (2006.01) |
| *A61F 2/44* | (2006.01) |
| *A61B 17/80* | (2006.01) |
| *A61B 17/86* | (2006.01) |
| *A61F 2/30* | (2006.01) |

(52) U.S. Cl.
CPC ...... *A61B 17/7059* (2013.01); *A61B 17/8057* (2013.01); *A61B 17/863* (2013.01); *A61F 2/30749* (2013.01); *A61F 2/44* (2013.01); *A61F 2/442* (2013.01); *A61F 2/447* (2013.01); *A61F 2/4455* (2013.01); *A61F 2/4465* (2013.01); *A61B 17/8047* (2013.01); *A61F 2002/3079* (2013.01); *A61F 2002/30187* (2013.01); *A61F 2002/30352* (2013.01); *A61F 2002/30364* (2013.01); *A61F 2002/30365* (2013.01); *A61F 2002/30367* (2013.01); *A61F 2002/30487* (2013.01); *A61F 2002/30528* (2013.01); *A61F 2002/30538* (2013.01); *A61F 2002/30593* (2013.01); *A61F 2002/30604* (2013.01); *A61F 2002/30787* (2013.01); *A61F 2310/00796* (2013.01)

(58) Field of Classification Search
CPC ... A61B 17/7059; A61B 17/8057; A61F 2/44; A61F 2/4455; A61F 2002/4475; A61F 2002/448; A61F 2002/4485; A61F 2002/449; A61F 2002/30187; A61F 2002/30364; A61F 2002/30367; A61F 2002/30538; A61F 2002/30365
See application file for complete search history.

(56) References Cited

U.S. PATENT DOCUMENTS

| | | |
|---|---|---|
| 5,401,269 A | 3/1995 | Buttner-Janz et al. |
| 6,039,763 A | 3/2000 | Shelokov |

(Continued)

*Primary Examiner* — Larry E Waggle, Jr.

(57) ABSTRACT

Intervertebral endoprosthesis discs suitable for surgical implantation between two vertebrae having and methods thereof. The prosthetic disc may have an endoprosthesis body including an anterior region and a posterior region designed to be positioned between a first vertebra and a second vertebra with a first and second movable insert positioned rotatably in anterior cavities and is rotatable to adjust the fasteners.

16 Claims, 9 Drawing Sheets

Related U.S. Application Data continuation of application No. 14/927,627, filed on Oct. 30, 2015, now Pat. No. 9,539,105, which is a continuation of application No. 14/474,528, filed on Sep. 2, 2014, now Pat. No. 9,198,775, which is a continuation of application No. 13/352,534, filed on Jan. 18, 2012, now Pat. No. 8,852,281.

(60) Provisional application No. 61/433,791, filed on Jan. 18, 2011.

(56) References Cited

U.S. PATENT DOCUMENTS

| | | |
|---|---|---|
| 6,679,883 B2 | 1/2004 | Hawkes et al. |
| 6,846,328 B2 | 1/2005 | Cauthen |
| 7,063,701 B2 | 6/2006 | Michelson |
| 7,507,240 B2 | 3/2009 | Olsen |
| 8,852,281 B2 | 10/2014 | Phelps |
| 2004/0193269 A1 | 9/2004 | Fraser |
| 2004/0220570 A1 | 11/2004 | Frigg |
| 2005/0085913 A1 | 4/2005 | Fraser et al. |
| 2005/0228386 A1 | 10/2005 | Ziolo et al. |
| 2005/0261688 A1 | 11/2005 | Grady |
| 2008/0027439 A1* | 1/2008 | Sasing ............... A61B 17/8047 606/279 |
| 2008/0234752 A1 | 9/2008 | Dahners |
| 2008/0300634 A1 | 12/2008 | Gray |
| 2008/0306550 A1 | 12/2008 | Matityahu |
| 2009/0157121 A1* | 6/2009 | Harris ............... A61B 17/8047 606/301 |
| 2010/0217393 A1 | 8/2010 | Theofilos |
| 2010/0249935 A1 | 9/2010 | Slivka |

\* cited by examiner

ARTIFICIAL SPINAL DISK PROSTHESIS

CROSS REFERENCE TO RELATED APPLICATIONS

This application is a continuation of U.S. patent application Ser. No. 16/865,510, filed May 4, 2020 (published as U.S. Pat. Pub. No. 2020-0305934), which is a continuation of U.S. patent application Ser. No. 16/046,000, filed Jul. 26, 2018, now U.S. Pat. No. 10,716,599, which is a continuation of U.S. patent application Ser. No. 15/367,456, filed Dec. 2, 2016, now U.S. Pat. No. 10,034,763, which is a continuation of U.S. patent application Ser. No. 14/927,627, filed Oct. 30, 2015, now U.S. Pat. No. 9,539,105, which is a continuation of U.S. patent application Ser. No. 14/474,528, filed Sep. 2, 2014, now U.S. Pat. No. 9,198,775, which is a continuation of U.S. patent application Ser. No. 13/352,534, filed Jan. 18, 2012, now U.S. Pat. No. 8,852,281, which claims priority to provisional Application No. 61/433,791, filed Jan. 18, 2011. These applications are incorporated herein by reference in their entireties for all purposes.

FIELD OF THE INVENTION

The present invention relates in general to the field of artificial prosthesis, and more particularly, to an improved artificial prosthesis for use in spinal joints with reduced material fatigue and improved patient comfort.

BACKGROUND OF THE INVENTION

Without limiting the scope of the invention, its background is described in connection with spinal joint prosthesis. A variety of artificial prosthesis are used to replace chronically injured or ruptured intervertebral discs and range from plate inserts, ball and socket joints, gel filled enclosures, spring-biased plates, plate and joint combinations and others.

For example, U.S. Pat. No. 6,846,328, issued to Cauthen teaches another articulating spinal implant. The articulating intervertebral disc replacement implant is formed from two elements, each engaging one of an adjacent pair of vertebra and capable of an articulating motion that resists compression and lateral movement between the vertebra, but allows the adjacent vertebra to articulate about an instantaneous axis of rotation.

Another example is taught in U.S. Pat. No. 6,039,763, discloses articulating spinal disc prosthesis that is designed to articulate in a manner resembling a human knee articulation. Briefly, the artificial spinal disc includes two plates each having a planar outer surface and an articulating inner surface. The planar outer surfaces contact and are affixed to adjacent inferior and superior surfaces of two adjacent vertebrae. The interior articulating surfaces of the artificial spinal disc are shaped generally to have one or more complementary convex/concave shaped articulating portions that are shaped and articulate in a manner similar to a human knee.

Another example of intervertebral disc prosthesis is taught in U.S. Pat. No. 5,401,269, which discloses an intervertebral disc endoprosthesis that includes two prosthesis plates that have a prosthesis core that cooperates with at least one prosthesis plate via an articulating surface permitting a rotational movement. The two plates are connected to the end plates of adjacent vertebrae. To control rotational movement around the vertical axis, the articulating surface forms curved arches of different average radius in the median section and in the frontal section. The radius of curvature in the sagittal section is less than in the frontal section.

SUMMARY OF THE INVENTION

The present invention provides an intervertebral endoprosthesis disc for surgical implantation between two vertebrae having an endoprosthesis body comprising an anterior region and a posterior region designed to be positioned between a first vertebra and a second vertebra; at least a first anterior cavity and a second anterior cavity positioned in the anterior region; a first movable insert having a first fastener aperture and positioned rotatably in the first anterior cavity, wherein the first movable insert is rotatable in the first anterior cavity; and a second movable insert having a second fastener aperture and positioned rotatably in the second anterior cavity, wherein the second movable insert is rotatable in the second anterior cavity independent of the first movable insert; and wherein a first insertion angle of a first fastener extending through the first fastener aperture may be adjusted by rotating the first movable insert and a second insertion angle of a second fastener extending through the second fastener aperture may be adjusted by rotating the second movable insert.

The present invention also provides a surgical cage for surgical implantation between two vertebrae of a spinal column, said surgical cage having a body that may be secured to a vertebra with a surgical screw; a first structure within the body for increasing an angle at which a first surgical screw may be screwed into a vertebra that is adjacent to a top the body; and a second structure within the body for increasing an angle at which a second surgical screw may be screwed into a vertebra that is adjacent to a bottom the body. The first structure comprises portions that define an aperture through the first structure for receiving the first surgical screw; the second structure comprises portions that define an aperture through the second structure for receiving the second surgical screw; a portion of the body that defines apertures through the body for receiving the first structure and the second structure; wherein the first structure is rotatably mounted with respect to the body to allow the aperture though the first structure to be rotated to increase an angle at which the first surgical screw may be screwed into the vertebra that is adjacent to the top of the body, and wherein the second structure is rotatably mounted with respect to the body to allow the aperture though the second structure to be rotated to increase an angle at which the second surgical screw may be screwed into the vertebra that is adjacent to the bottom of the body.

The first structure having portions that define an aperture through the first structure for receiving the first surgical screw comprises a portion of first cylindrically shaped shell that is rotatably mounted on the body; and the second structure having portions that define an aperture through the second structure for receiving the second surgical screw comprises a portion of second cylindrically shaped shell that is rotatably mounted on the body.

An vertebral prosthesis for surgical implantation across at least two vertebrae having a first attachment fixture and a second attachment fixture each attachment fixture comprising an anterior region and a posterior region designed to be positioned on the surface of a first vertebra, at least a first anterior cavity and a second anterior cavity positioned in the anterior region, a first movable insert having a first fastener aperture and positioned rotatably in the first anterior cavity, wherein the first movable insert is rotatable in the first anterior cavity, and a second movable insert having a second fastener aperture and positioned rotatably in the second anterior cavity, wherein the second movable insert is rotatable in the second anterior cavity independent of the first movable insert, wherein a first insertion angle of a first fastener extending through the first fastener aperture may be adjusted by rotating the first movable insert and a second insertion angle of a second fastener extending through the second fastener aperture may be adjusted by rotating the second movable insert; and an stabilization body attached to the first and the second attachment fixtures to extend from the first vertebra to the second vertebra.

The present invention also provides a method of stabilizing a two or more vertebra by positioning an intervertebral endoprosthesis between two vertebrae, wherein the intervertebral endoprosthesis comprises: an endoprosthesis body comprising an anterior region and a posterior region designed to be positioned between a first vertebra and a second vertebra, at least a first anterior cavity and a second anterior cavity positioned in the anterior region, a first movable insert having a first fastener aperture and positioned rotatably in the first anterior cavity, wherein the first movable insert is rotatable in the first anterior cavity, and a second movable insert having a second fastener aperture and positioned rotatably in the second anterior cavity, wherein the second movable insert is rotatable in the second anterior cavity independent of the first movable insert; inserting a first fastener through the first fastener aperture; adjusting a first insertion angle of a first fastener extending through the first fastener aperture by rotating the first movable insert; inserting the first fastener into the first vertebra; securing a second fastener through the second fastener aperture; adjusting a second insertion angle of the second fastener extending through the second fastener aperture by rotating the second movable insert; and securing a second fastener through the second fastener aperture.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
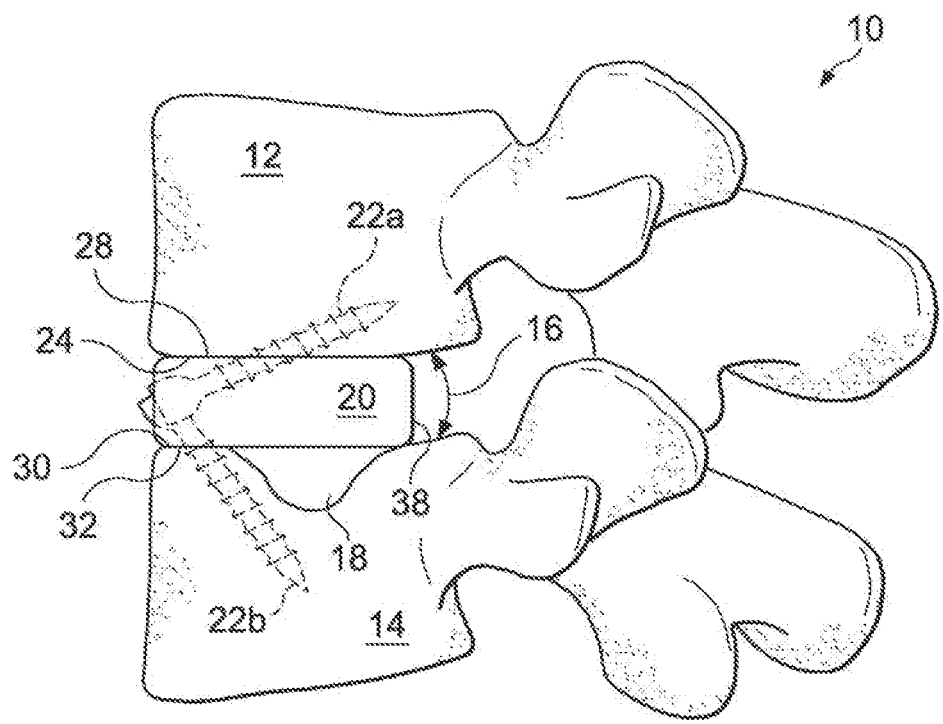
FIGS. 1A and 1B are side views of the intervertebral disc endoprosthesis in operation.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The spine encloses the spinal cord and includes thirty-three vertebrae. The vertebrae are divided into four regions that include the uppermost seven vertebrae referred to as the cervical vertebrae, followed sequentially by the twelve thoracic vertebrae, the five lumbar vertebrae and the five sacral vertebrae. The final four vertebrae are referred to as the coccygeal vertebrae.

Although the vertebrae of each region have a different structure, the basic vertebra structure has certain similarities. The vertebral body is the anterior part of the vertebra and is roughly cylindrical. The vertebral body has a superior surface that is concave transversely and convex antero-posteriorly with prominent elevations on each side. Two articular facets on the inferior surface of the body articulate with the uncinate processes. Additionally, the posterior arch is formed by the pedicles, the articular processes, the laminae and the spinous processes. The vertebral pedicles are short and thick regions projecting backwards and slightly laterally from the vertebral body. The articular processes are located at the junction of the pedicles and laminae and are made up of the superior articular process that articulates with the above vertebra and the inferior articular process that articulates with the vertebra below it. The laminae are long and thin, extending backwards and medially from the pedicle to meet the midline thereby completing the posterior arch. The spinous processes project backwards from the junction of the laminae. Transverse processes arise anteriorly from the vertebral body and posteriorly from the articular processes to form the vertebral foramen. The vertebral foramen is the triangular region occupied by the spinal cord, meninges and associated vessels. Additionally, the vertebrae cephalad to the sacral vertebrae are united by articular capsules and by ligaments and separated by fibrocartilaginous intervertebral discs. The outside surface of the vertebral body is made of a relatively strong cortical bone layer, while the center of the vertebral body is made of a weak cancellous bone.

The vertebral bodies are separated by intervertebral discs, which provide the majority of the weight bearing support of the vertebral column. The intervertebral discs include a cartilage shell enclosing a central mass that provides cushioning and dampening of compressive forces applied to the vertebral bodies and the spinal column. Generally, the central mass is relatively inelastic, but can bulge outward to accommodate loads applied axially to the spinal.

The successive positioning of the vertebral body allows the vertebral foramen to surround the spinal cord and retain articulation of the vertebrae and extend posteriorly of the spinal canal. The complicated vertebral structure, the degree of spinal articulation and complicated network of connective elements make the spine susceptible to many forms of damage, e.g., traumatic spinal injuries, tumors, infections, surgeries, disease processes, aging processes, and congenital abnormalities. Various types of spinal column disorders are known and include degenerative disc disease, excess lordosis (abnormal backward curvature of the spine), fractured vertebra, kyphosis (abnormal forward curvature of the spine), ruptured discs, scoliosis (abnormal lateral curvature of the spine), slipped discs, spondylolisthesis (abnormal forward displacement of vertebra) and the like.

The discs of the present invention may be fabricated from generally biocompatible materials including, without limitation, titanium, surgical alloys, stainless steel, chrome-molybdenum alloy, cobalt chromium alloy, zirconium oxide ceramic, non-absorbable polymers and other anticipated biocompatible metallic, ceramic or polymeric materials and combinations thereof. The discs may be fabricated from different materials and may even be fabricated by using different materials within each disc. Certain materials may even be used to coat a portion or all of a disc, e.g., a titanium disc may be fused, welded, melted, coated, impregnated or infused along it's a portion or all of its periphery with a ceramic or a polymer. Alternatively, the fused, welded, melted, coated, impregnated or infused material may be on a portion or all of one surface but not another, or, may completely surround the disc.

The components of the present invention may be constructed from any suitable similar or dissimilar materials (e.g., titanium, a titanium alloy, a metal, an alloy, a stainless steel, a composite, a polymer, a blend of polymers, a carbon fiber, a plastic, a thermoplastic, a ceramic, carbon nanotubes, a synthetic material or other material known to the skilled artisan) depending on the particular need or application. In addition combinations and mixtures of material may be used, e.g., ceramic coated metal, carbon nanotube coated metal and/or ceramic, polymer coated metal and/or ceramic, a magnetic material combined with a polymer, an electrically conductive material combined with a polymer, metal, plastic, etc. and so-forth. For example, polymers and many lightweight and remarkably strong materials that include a reinforced two-phase material, carbon fiber reinforced plastic, carbon fiber, plastic, polymers or combinations thereof. Polymers such as silicone, polyethylene, nylon, vinyl, methylmethacyrate, dacrons or teflon may be used. The screws may be made of a strong material (e.g., metal, magnamite graphite fiber, carbon reinforced plastic) so as to prevent the screws from being sheared off by the stress of the system. Additionally, porous material in which the porosity is controlled by the replamine form process may be used. The materials used are not limited to the above noted and may also include other suitable solid materials that have the above-noted properties.

The figures depict specific embodiments of the present invention used as an artificial spinal disc replacement. As will be disclosed in detail herein, the present invention will have wide applicability to a number of different locations and for replacement of many different types of joints. The artificial spinal prosthesis depicted in the figures are non-limiting examples of the present invention. In addition the present invention includes embodiments that are used in other locations in the body and various cages. The variable angle attachment mechanism of the present invention may be used in various medical devices known to the skilled artisan.

FIG. 1A is an image of the intervertebral disc endoprosthesis in operation 10. The image illustrates two vertebrae, superior vertebra 12 and inferior vertebra 14 of the spine separated by a gap 16 showing eroded region 18. The intervertebral disc endoprosthesis 20 is positioned in the gap 16 and secured to the superior vertebra 12 and inferior vertebra 14 using fasteners 22a and 22b. The superior vertebra 12 has an inferior surface 24 depicted as planar, or flat, so as to optimize the substantially complementary upper surface 28 of the disc endoprosthesis 20. The inferior vertebra 14 has a superior vertebral surface 30 that has a shape that is complementary to the inferior surface 32 of the disc endoprosthesis 20. Although not shown, the musculature and other body tissues normally surround the spinal column around the disc endoprosthesis 20 and the superior vertebra 12 and inferior vertebra 14. A wide variety of mechanical attachments methods and hardware may be used ensure that the components of the disc endoprosthesis 20 remain in place for the duration of their use. By way of example and without limitation, mechanical attachment may include a screw, nail, rivet, adhesive, wire, band, strap, and embodiments for porous coating of the prosthesis endplate screws or the combination and locking mechanisms to affix the screw to the disc endoprosthesis 20. The disc endoprosthesis 20 may be adapted to receive and retain screws, nails, rivets, spikes and other articles used to secure the disc endoprosthesis 20 to adjacent vertebra without protruding from the surface of the discs to cause friction. For example, the intervertebral disc endoprosthesis 20 may include countersunk fastener 22 or can have locking methods or mechanisms that stabilize a screw (fasteners 22a and 22b) to the disc endoprosthesis 20.

Figure 1B:
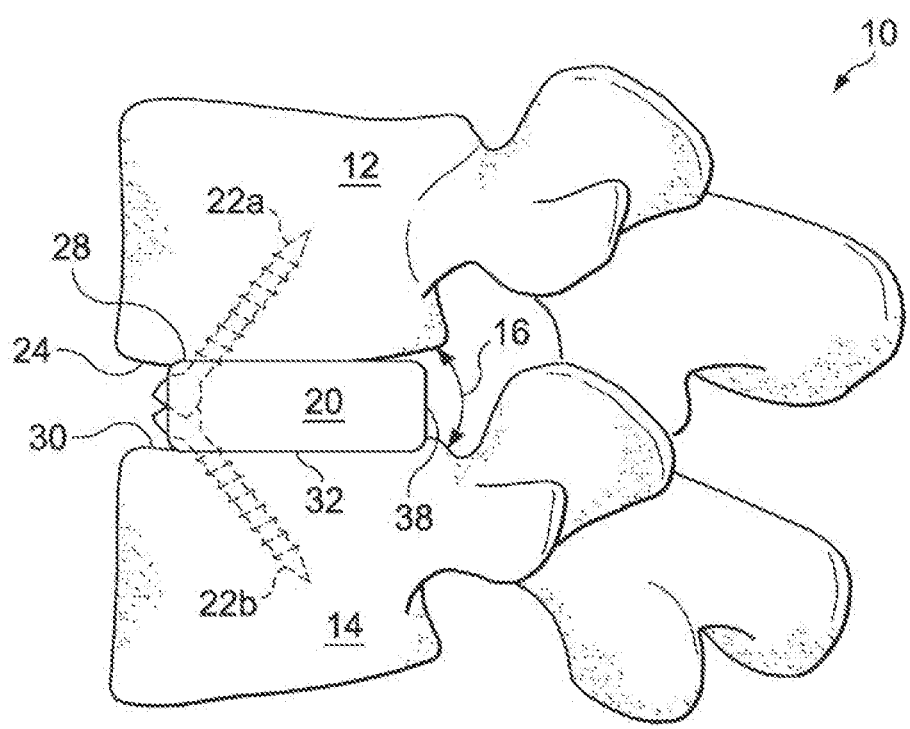

FIG. 1B is an image of the intervertebral disc endoprosthesis in operation 10 illustrating the need for a steeper insertion angle as a result of the smaller vertebra. The image illustrates two vertebrae, superior vertebra 12 and inferior vertebra 14 of the spine separated by a gap 16 showing eroded region 18. The intervertebral disc endoprosthesis 20 is positioned in the gap 16 and secured to the superior vertebra 12 and inferior vertebra 14 using fasteners 22a and 22b. The superior vertebra 12 has an inferior surface 24 depicted as planar, or flat, so as to optimize the substantially complementary upper surface 28 of the disc endoprosthesis 20. The inferior vertebra 14 has a superior vertebral surface 30 that has a shape that is complementary to the inferior surface 32 of the disc endoprosthesis 20. Although not shown, the musculature and other body tissues normally surround the spinal column around the disc endoprosthesis 20 and the superior vertebra 12 and inferior vertebra 14. A wide variety of mechanical attachments methods and hardware may be used ensure that the components of the disc endoprosthesis 20 remain in place for the duration of their use. By way of example and without limitation, mechanical attachment may include a screw, nail, rivet, adhesive, wire, band, strap, and embodiments for porous coating of the prosthesis endplate screws or the combination and locking mechanisms to affix the screw to the disc endoprosthesis 20. The disc endoprosthesis 20 may be adapted to receive and retain screws, nails, rivets, spikes and other articles used to secure the disc endoprosthesis 20 to adjacent vertebra without protruding from the surface of the discs to cause friction. For example, the intervertebral disc endoprosthesis 20 may include countersunk fastener 22 or can have locking methods or mechanisms that stabilize a screw (fasteners 22a and 22b) to the disc endoprosthesis 20.

Figure 2:
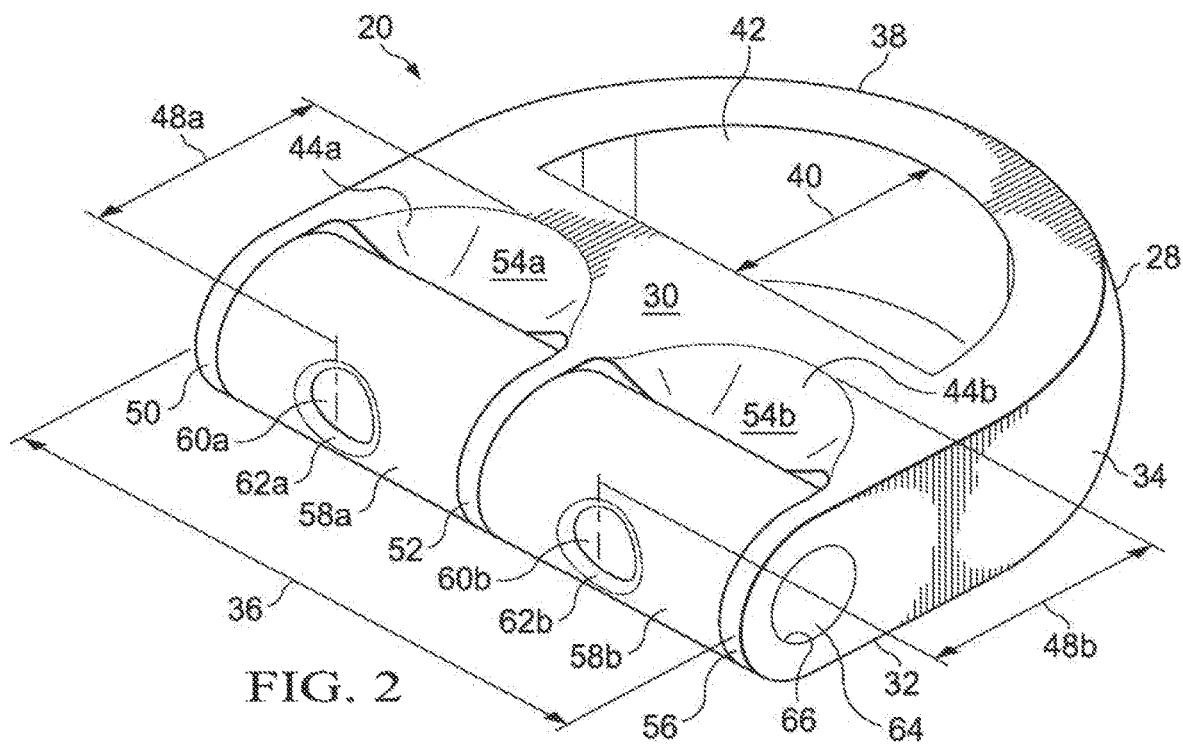
FIG. 2 is an image of the intervertebral disc endoprosthesis of the present invention.

FIG. 2 is an image of the intervertebral disc endoprosthesis 20 of the present invention. The disc endoprosthesis 20 includes a superior vertebral surface 30 an inferior surface 32 and a side surface 34 that extends between the superior vertebral surface 30 an inferior surface 32 to separate them. The disc endoprosthesis 20 includes an anterior region 36 that is generally flat and the posterior region 38 that is arched. Optionally the present invention may have a recess 40 having an arched parameter 42 that extends to form the recess 40 in some embodiments the recess 40 extends through the disc endoprosthesis 20. However, in other embodiments the recess 40 is extends partially through the disc endoprosthesis 20 or creates an indention (not shown) into the disc endoprosthesis 20. The anterior region 36 includes a first anterior cavity 44a formed by a first cavity width 46a and a first cavity length 48a relative to the first bridge 50 and the middle bridge 52. The first anterior cavity 44a may include a first tapered region 54a extending toward the anterior region 36. The anterior region 36 also includes a second anterior cavity 44b formed by a second cavity width 46b and a second cavity length 48b relative to the second bridge 56 and the middle bridge 52. The second anterior cavity 44b may include a second tapered region 54b extending toward the anterior region 36. A first insert 58a is rotatably positioned within the first anterior cavity 44a extending from the first bridge 50 to the middle bridge 52 and away from the anterior region 36 toward the first tapered region 54a. The first insert 58a includes a first insert aperture 60a extending through the first insert 58a to accept a fastener (not shown) and including a first insert taper 62a to allow the fastener (not shown) to be recessed into the first insert 58a. A second insert 58b is rotatably positioned within the second anterior cavity 44b extending from the second bridge 56 to the middle bridge 52 and away from the anterior region 36 toward the second tapered region 54b. The second insert 58b includes a second insert aperture 60b extending through the second insert 58b to accept a fastener (not shown) and including a second insert taper 62b to allow the fastener (not shown) to be recessed into the second insert 58b. The second insert 58b may be secured in the second anterior cavity 44b and rotatable through the mating of a securing peg 64 and a securing aperture 66.

The recess 40 forms a cavity for inserting bone graph material. In some embodiments the cavity extends through the disc endoprosthesis 20. However, other embodiments may be a cavity or an indention on one or both sides depending on the particular application. In addition the recess 40 may be of a variety of sizes, depths and shapes. Regardless of the actual parameters of the recess 40, the skilled artisan will understand that bone graph materials and/or materials that support or enhance bone graphing may be in the recess 40. For example, the bone graft material serves as a scaffold for new bone growth that is perpetuated by the native bone; osteoprogenitor cells can be stimulated to differentiate into osteoblasts that then begin new bone formation. Osteopromotion may also be used, e.g., the enhancement of osteoinduction without the possession of osteoinductive properties. For example, enamel matrix derivative has been shown to enhance the osteoinductive effect of demineralized freeze dried bone allograft (DFDBA), but will not stimulate de novo bone growth alone. The material may be an autologous (or autogenous) bone grafting involves utilizing bone obtained from the same individual receiving the graft. Bone can be harvested from non-essential bones, such as from the iliac crest, or more commonly in oral and maxillofacial surgery, from the mandibular symphysis (chin area) or anterior mandibular ramus (the coronoid process). Allograft bone, like autogenous bone, is derived from humans; the difference is that allograft is harvested from an individual other than the one receiving the graft. Types of bone allograft includes fresh or fresh-frozen bone, freeze-dried bone allograft (FDBA), and demineralized freeze-dried bone allograft (DFDBA). In addition, artificial bone material can be used, e.g., ceramics such as calcium phosphates (e.g. hydroxyapatite and tricalcium phosphate), Bioglass and calcium sulphate; all of which are biologically active to different degrees depending on solubility in the physiological environment. These materials can be doped with growth factors, ions such as strontium or mixed with bone marrow aspirate to increase biological activity. Xenografts including a calcified matrix may be used. Alloplastic grafts may be made from hydroxylapatite. Some synthetic bone grafts are made of calcium carbonate or tricalcium phosphate and in combination with hydroxylapatite. In addition the recess 40 may include one or more factors to enhance and stimulate the growth of bones, e.g., a growth Factor enhanced graft, e.g., Human Growth Factors or Morphogens (Bone Morphogenic Proteins in conjunction with a carrier medium, such as collagen).

Figure 3:
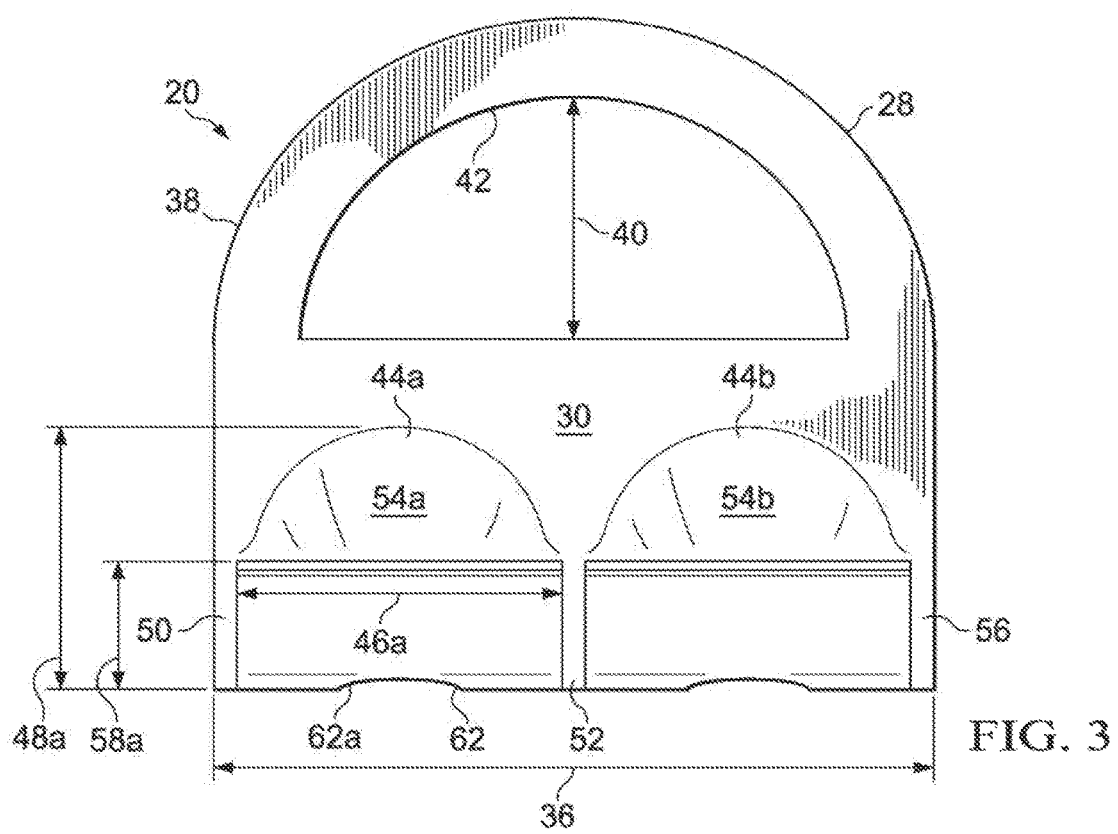
FIG. 3 is a top view of the intervertebral disc endoprosthesis of the present invention.

FIG. 3 is a top view of an image of the intervertebral disc endoprosthesis 20 of the present invention. The disc endoprosthesis 20 includes a superior vertebral surface 30 an inferior surface (not shown) and a side surface (not shown) that extends between the superior vertebral surface 30 an inferior surface (not shown) to separated them. The disc endoprosthesis 20 includes an anterior region 36 that is generally flat and the posterior region 38 that is arched. Optionally the present invention may have a recess 40 having an arched parameter 42 that extends to form the recess 40. In some embodiments, the recess 40 extends through the disc endoprosthesis 20; however, in other embodiments the recess 40 is extends partially through the disc endoprosthesis 20 or creates an indention (not shown) into the disc endoprosthesis 20. The anterior region 36 includes a first anterior cavity 44a formed by a first cavity width 46a and a first cavity length 48a relative to the first bridge 50 and the middle bridge 52. The first anterior cavity 44a may include a first tapered region 54a extending toward the anterior region 36. The anterior region 36 also includes a second anterior cavity 44b formed by a second cavity width 46b and a second cavity length 48b relative to the second bridge 56 and the middle bridge 52. The second anterior cavity 44b may include a second tapered region 54b extending toward the anterior region 36. A first insert 58a is rotatably positioned within the first anterior cavity 44a extending from the first bridge 50 to the middle bridge 52 and away from the anterior region 36 toward the first tapered region 54a. The first insert 58a includes a first insert aperture (not shown) extending through the first insert 58a to accept a fastener (not shown) and including a first insert taper 62a to allow the fastener (not shown) to be recessed into the first insert 58a. A second insert 58b is rotatably positioned within the second anterior cavity 44b extending from the second bridge 56 to the middle bridge 52 and away from the anterior region 36 toward the second tapered region 54b. The second insert 58b includes a second insert aperture (not shown) extending through the second insert 58b to accept a fastener (not shown) and including a second insert taper 62b to allow the fastener (not shown) to be recessed into the second insert 58*b*. The second insert 58*b* may be secured in the second anterior cavity 44*b* and rotatable through the mating of a securing peg (not shown) and securing aperture (not shown).

Figure 4:
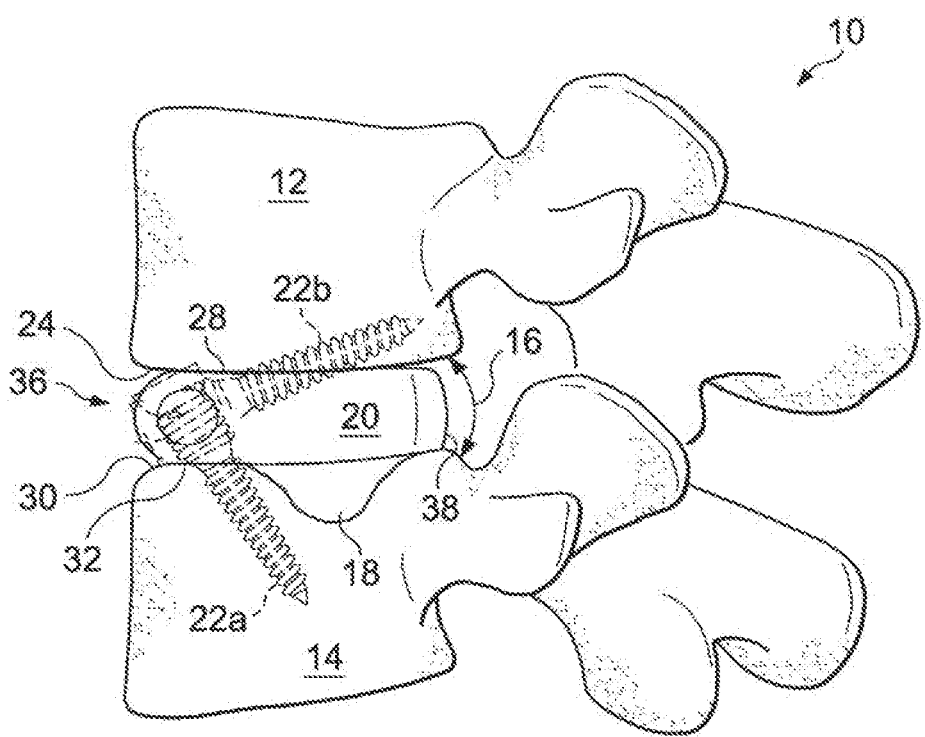
FIG. 4 is an image of the intervertebral disc endoprosthesis in operation of the present invention in operation.

FIG. 4 is an image of the intervertebral disc endoprosthesis in operation 10 of the present invention in operation. The image illustrates two superior vertebra 12 and inferior vertebra 14 of the spine separated by a gap 16 showing eroded region 18. The intervertebral disc endoprosthesis 20 is positioned in the gap 16 and secured to the superior vertebra 12 and inferior vertebra 14 using fasteners 22*a* and 22*b*. The superior vertebra 12 has an inferior surface 24 depicted as planar, or flat, so as to optimize the substantially complementary upper surface 28 of the disc endoprosthesis 20. The inferior vertebra 14 has a superior vertebral surface 30 that has a shape that is complementary to the inferior surface 32 of the disc endoprosthesis 20. For example, the intervertebral disc endoprosthesis 20 the first insert (not shown) having a first insert aperture (not shown) extending through the first insert (not shown) to accept a first fastener 22*a* and including a first insert taper (not shown) to allow the fastener 22*a* to be recessed into the first insert (not shown). A second insert (not shown) is rotatably positioned within the second anterior cavity (not shown) extending from the second bridge (not shown) to the middle bridge (not shown) and away from the anterior region 36 toward the second tapered region (not shown). The second insert 58*b* includes a second insert aperture 60*b* extending through the second insert 58*b* to accept a fastener (not shown) and including a second insert taper 62*b* to allow the fastener (not shown) to be recessed into the second insert 58*b*. The intervertebral disc endoprosthesis 20 includes a first and a second countersunk fastener 22*a* and 22*b* to secure the intervertebral disc endoprosthesis 20 to the disc endoprosthesis 20 depicted in FIG. 1.

Figure 5:
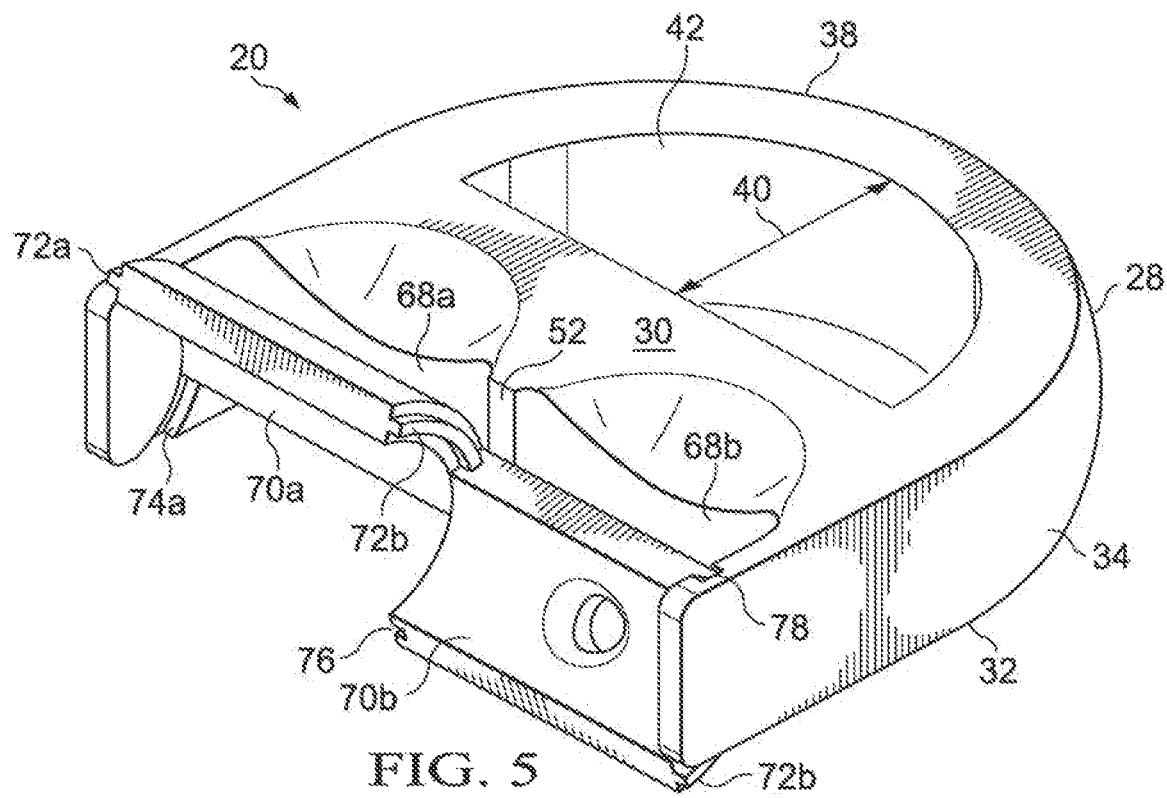
FIG. 5 is another image of the intervertebral disc endoprosthesis of the present invention.

FIG. 5 is an image of the intervertebral disc endoprosthesis 20 of the present invention. The disc endoprosthesis 20 includes a superior vertebral surface 30 an inferior surface 32 and a side surface 34 that extends between the superior vertebral surface 30 an inferior surface 32 to separate them. The disc endoprosthesis 20 includes an anterior region 36 that is generally flat and the posterior region 38 that is arched. Optionally the present invention may have a recess 40 having an arched parameter 42 that extends to form the recess 40 in some embodiments the recess 40 extends through the disc endoprosthesis 20. However, in other embodiments the recess 40 is extends partially through the disc endoprosthesis 20 or creates an indention (not shown) into the disc endoprosthesis 20. The anterior region 36 includes a first anterior cavity 44*a* formed by a first cavity width 46*a* and a first cavity length 48*a* relative to the first bridge 50, the middle bridge 52 and the first tapered region edge 68*a*. The first anterior cavity 44*a* may include a first tapered region 54*a* extending toward the anterior region 36. The anterior region 36 also includes a second anterior cavity 44*b* formed by a second cavity width 46*b* and a second cavity length 48*b* relative to the second bridge 56 and the middle bridge 52. The second anterior cavity 44*b* may include a second tapered region 54*b* extending toward the anterior region 36. A first insert 58*a* having a first insert arched surface 70*a* is rotatably positioned within the first anterior cavity 44*a* extending from the first bridge 50 to the middle bridge 52. The first insert 58*a* includes a first insert first tongue 72*a* that mates to a first bridge groove 74*a* positioned in the first bridge 50 and a first insert second tongue 72*b*. The first insert 58*a* includes a first insert aperture (not shown) extending through the first insert (not shown) to accept a fastener (not shown) and including a first insert taper (not shown) to allow the fastener (not shown) to be recessed into the first insert 58*a*. A second insert 58*b* is rotatably positioned within the second anterior cavity 44*b* extending from the second bridge 56 to the middle bridge 52 and away from the anterior region 36 toward the second tapered region 54*b* to the second tapered region edge 68*b*. The second insert 58*b* includes a second insert groove 76 that mates to the first insert second tongue 72*b* of the first insert 58*a* and a second insert first tongue 72*b* that mates to a second bridge groove 78 positioned in the second bridge 56. The second insert 58*b* includes a second insert aperture 60*b* extending through the second insert 58*b* to accept a fastener (not shown) and including a second insert taper 62*b* to allow the fastener (not shown) to be recessed into the second insert 58*b*.

Figure 6:
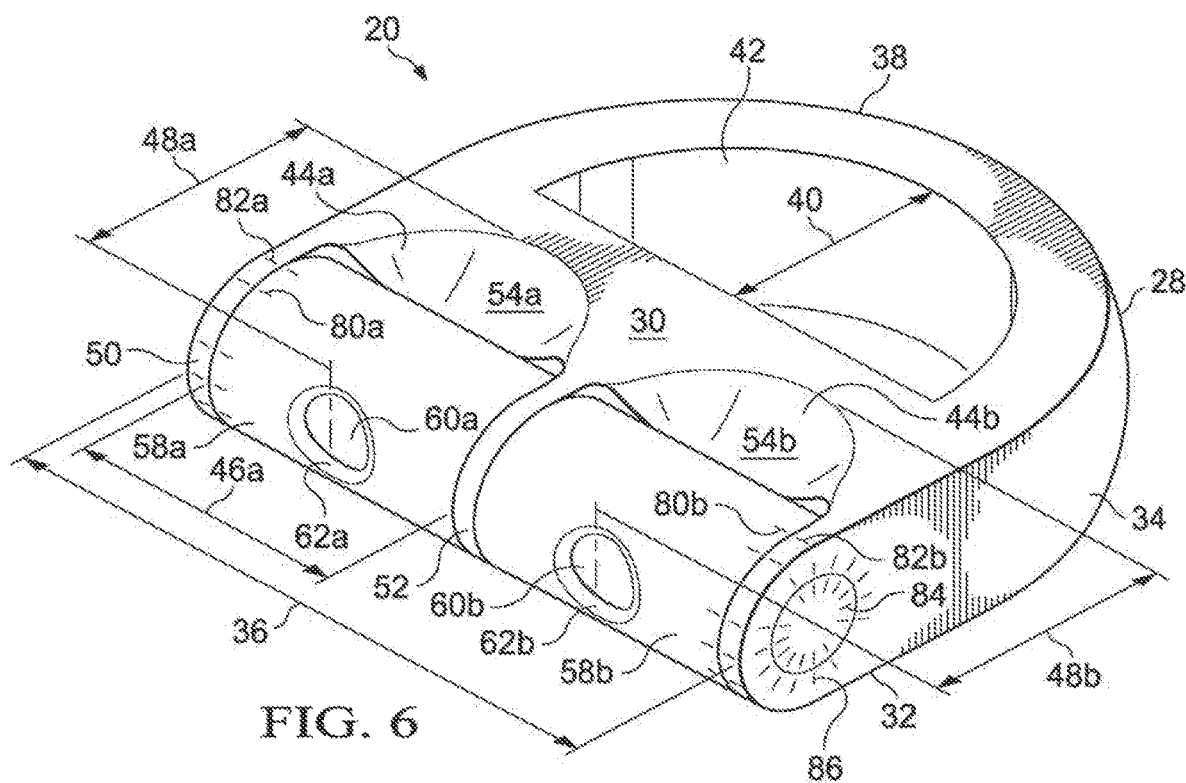
FIG. 6 is an image of the intervertebral disc endoprosthesis 20 of the present invention.

FIG. 6 is an image of the intervertebral disc endoprosthesis 20 of the present invention. The disc endoprosthesis 20 includes a superior vertebral surface 30 an inferior surface 32 and a side surface 34 that extends between the superior vertebral surface 30 an inferior surface 32 to separate them. The disc endoprosthesis 20 includes an anterior region 36 that is generally flat and the posterior region 38 that is arched. Optionally the present invention may have a recess 40 having an arched parameter 42 that extends to form the recess 40 in some embodiments the recess 40 extends through the disc endoprosthesis 20. However, in other embodiments the recess 40 is extends partially through the disc endoprosthesis 20 or creates an indention (not shown) into the disc endoprosthesis 20. The anterior region 36 includes a first anterior cavity 44*a* formed by a first cavity width 46*a* and a first cavity length 48*a* relative to the first bridge 50 and the middle bridge 52. The first anterior cavity 44*a* may include a first tapered region 54*a* extending toward the anterior region 36. The anterior region 36 also includes a second anterior cavity 44*b* formed by a second cavity width 46*b* and a second cavity length 48*b* relative to the second bridge 56 and the middle bridge 52. The second anterior cavity 44*b* may include a second tapered region 54*b* extending toward the anterior region 36. A first insert 58*a* is rotatably positioned within the first anterior cavity 44*a* extending from the first bridge 50 to the middle bridge 52 and away from the anterior region 36 toward the first tapered region 54*a*. The first insert 58*a* includes a first insert aperture 60*a* extending through the first insert 58*a* to accept a fastener (not shown) and including a first insert taper 62*a* to allow the fastener (not shown) to be recessed into the first insert 58*a*. A second insert 58*b* is rotatably positioned within the second anterior cavity 44*b* extending from the second bridge 56 to the middle bridge 52 and away from the anterior region 36 toward the second tapered region 54*b*. The second insert 58*b* includes a second insert aperture 60*b* extending through the second insert 58*b* to accept a fastener (not shown) and including a second insert taper 62*b* to allow the fastener (not shown) to be recessed into the second insert 58*b*. The second insert 58*b* may be secured in the second anterior cavity 44*b* and rotatable through the mating of a securing peg 64 and a securing aperture 66. The first insert 58*a* and the second insert 58*b* include first insert indicia 80*a* and second insert indicia 80*b* used to align or reference the first bridge indicia 82*a* and second bridge indicia 82*b* on the first bridge 50 and the second bridge 56. In addition, the securing peg 64 may include securing peg indicia 84 and the securing aperture 66 may include the corresponding securing aperture indicia 86 that may be used for alignment or reference.

Figure 7:
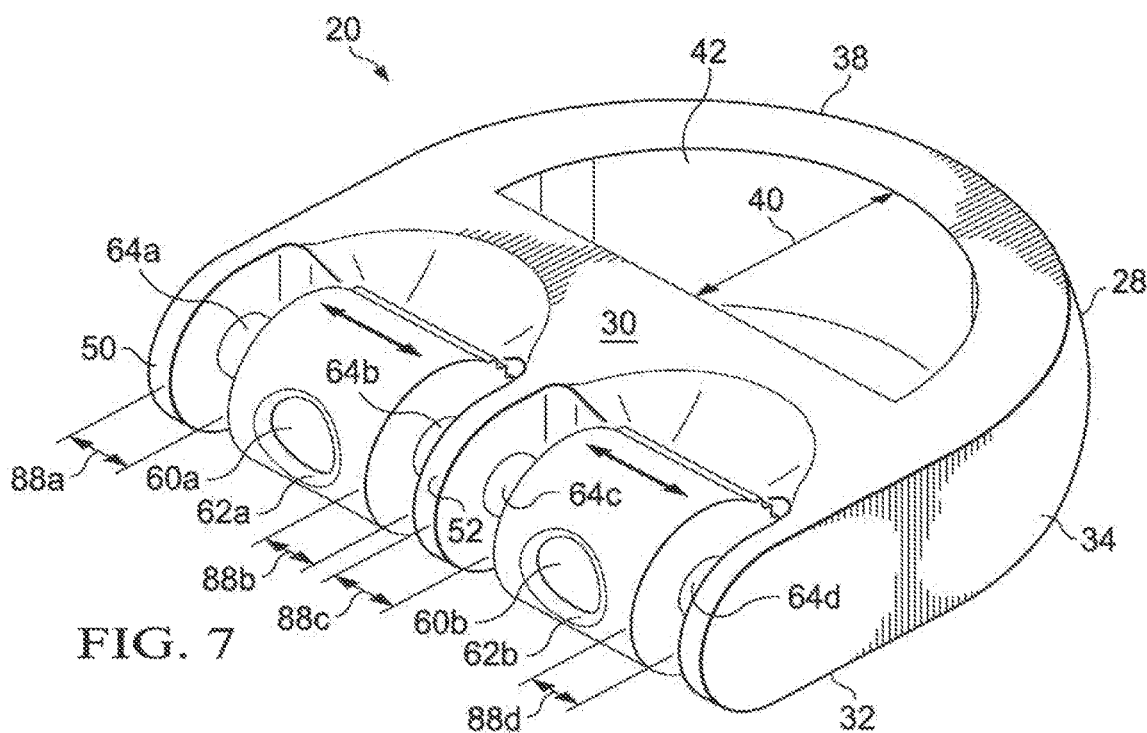
FIG. 7 is an image of another embodiment of the intervertebral disc endoprosthesis of the present invention.

FIG. 7 is an image of the intervertebral disc endoprosthesis 20 of the present invention. The disc endoprosthesis 20 includes a superior vertebral surface 30 an inferior surface 32 and a side surface 34 that extends between the superior vertebral surface 30 an inferior surface 32 to separate them. The disc endoprosthesis 20 includes an anterior region 36 that is generally flat and the posterior region 38 that is arched. Optionally, the present invention may have an recess 40 having an arched parameter 42 that extends to form the recess 40 in some embodiments the recess 40 extends through the disc endoprosthesis 20. However, in other embodiments the recess 40 is extends partially through the disc endoprosthesis 20 or creates an indention (not shown) into the disc endoprosthesis 20. The anterior region 36 includes a first anterior cavity 44a formed by a first cavity width 46a and a first cavity length 48a relative to the first bridge 50 and the middle bridge 52. The first anterior cavity 44a may include a first tapered region 54a extending toward the anterior region 36. The anterior region 36 also includes a second anterior cavity 44b formed by a second cavity width 46b and a second cavity length 48b relative to the second bridge 56 and the middle bridge 52. The second anterior cavity 44b may include a second tapered region 54b extending toward the anterior region 36. A first insert 58a is rotatably positioned within the first anterior cavity 44a extending from the first bridge 50 to the middle bridge 52 and away from the anterior region 36 toward the first tapered region 54a. The first insert 58a includes a first insert aperture 60a extending through the first insert 58a to accept a fastener (not shown) and including a first insert taper 62a to allow the fastener (not shown) to be recessed into the first insert 58a. A second insert 58b is rotatably positioned within the second anterior cavity 44b extending from the second bridge 56 to the middle bridge 52 and away from the anterior region 36 toward the second tapered region 54b. The second insert 58b includes a second insert aperture 60b extending through the second insert 58b to accept a fastener (not shown) and including a second insert taper 62b to allow the fastener (not shown) to be recessed into the second insert 58b. The second insert 58b may be secured in the second anterior cavity 44b and rotatable through the securing peg 64a, 64b, 64c, and 64d. The first insert 58a and the second insert 58b may be smaller than the corresponding first anterior cavity 44a and second anterior cavity 44b to provide the insert gaps 88a, 88b, 88c, and 88d.

Figure 8:
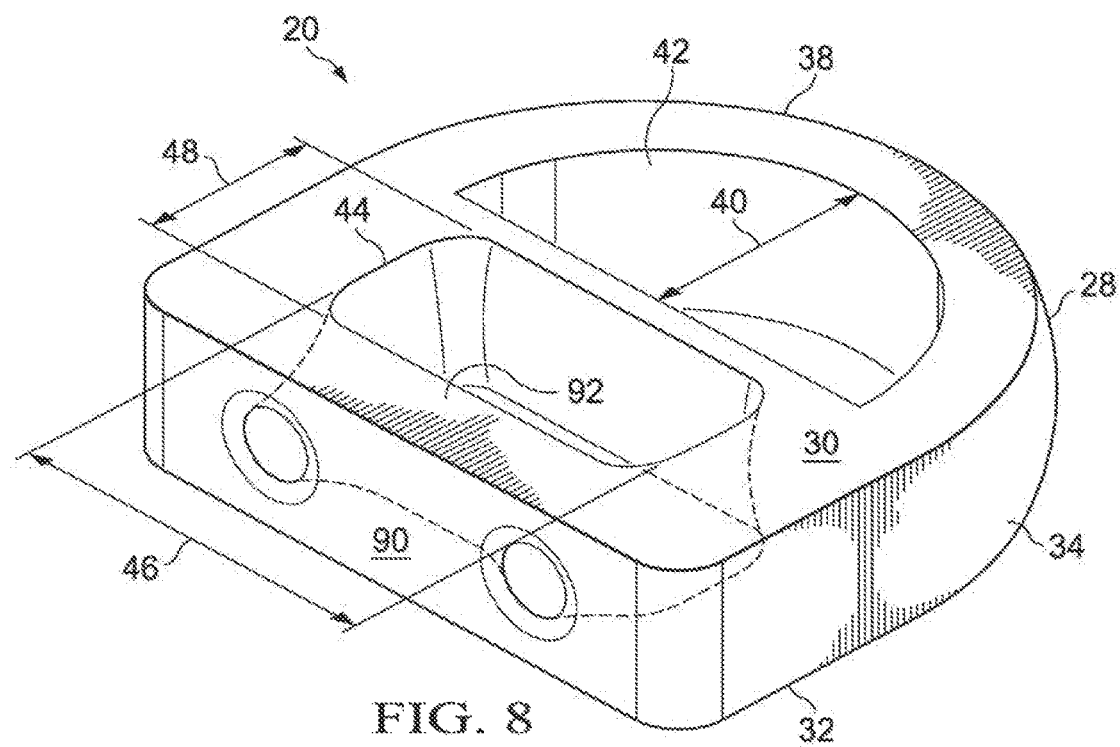
FIG. 8 is an image of another embodiment of the intervertebral disc endoprosthesis of the present invention.

FIG. 8 is an image of the intervertebral disc endoprosthesis 20 of the present invention. The disc endoprosthesis 20 includes a superior vertebral surface 30 an inferior surface 32 and a side surface 34 that extends between the superior vertebral surface 30 an inferior surface 32 to separate them. The disc endoprosthesis 20 includes an anterior region 36 that is generally flat and the posterior region 38 that is arched. Optionally the present invention may have a recess 40 having an arched parameter 42 that extends to form the recess 40 in some embodiments the recess 40 extends through the disc endoprosthesis 20. However, in other embodiments the recess 40 is extends partially through the disc endoprosthesis 20 or creates an indention (not shown) into the disc endoprosthesis 20. The anterior region 36 includes an anterior surface 90 and an first anterior cavity 44 formed by a first cavity width 46 and a first cavity length 48. The first anterior cavity 44 may include a first tapered region 92 extending toward the anterior region 36. The anterior surface 90 includes a first insert aperture 60a extending through the first insert 58a to accept a fastener (not shown) and including a first insert taper 62a and a second insert taper 62b to allow the fasteners (not shown) to be recessed.

Figure 9:
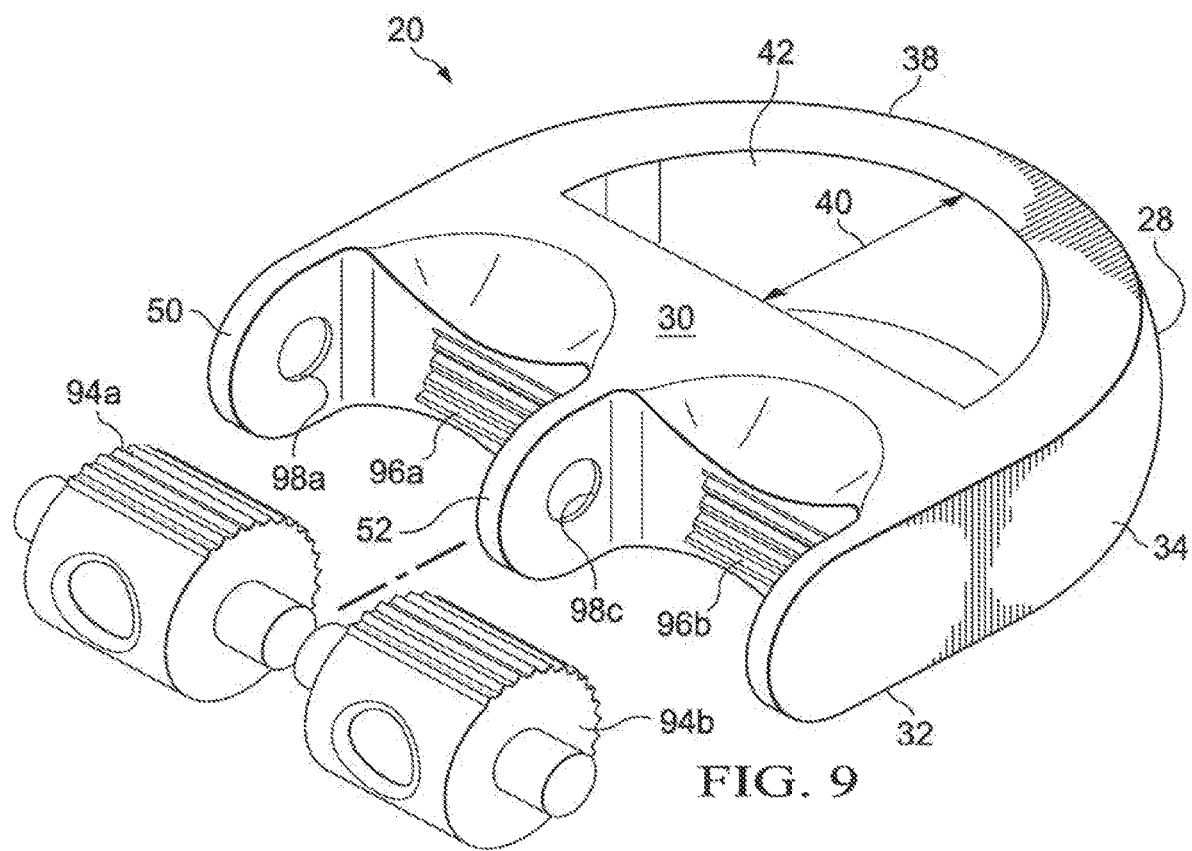
FIG. 9 is an image of another embodiment of the intervertebral disc endoprosthesis of the present invention.

FIG. 9 is an image of the intervertebral disc endoprosthesis 20 of the present invention. The disc endoprosthesis 20 includes a superior vertebral surface 30 an inferior surface 32 and a side surface 34 that extends between the superior vertebral surface 30 an inferior surface 32 to separate them. The disc endoprosthesis 20 includes an anterior region 36 that is generally flat and the posterior region 38 that is arched. Optionally the present invention may have an recess 40 having an arched parameter 42 that extends to form the recess 40 in some embodiments the recess 40 extends through the disc endoprosthesis 20. However, in other embodiments the recess 40 is extends partially through the disc endoprosthesis 20 or creates an indention (not shown) into the disc endoprosthesis 20. The anterior region 36 includes a first anterior cavity 44a formed by a first cavity width 46a and a first cavity length 48a relative to the first bridge 50 and the middle bridge 52. The first anterior cavity 44a may include a first tapered region 54a extending toward the anterior region 36. The anterior region 36 also includes a second anterior cavity 44b formed by a second cavity width 46b and a second cavity length 48b relative to the second bridge 56 and the middle bridge 52. The second anterior cavity 44b may include a second tapered region 54b extending toward the anterior region 36. A first insert 58a is rotatably positioned within the first anterior cavity 44a extending from the first bridge 50 to the middle bridge 52 and away from the anterior region 36 toward the first tapered region 54a. The first insert 58a includes a first insert aperture 60a extending through the first insert 58a to accept a fastener (not shown) and including a first insert taper 62a to allow the fastener (not shown) to be recessed into the first insert 58a. The first insert 58a includes a first insert grooved region 94a that mate to first insert aperture grooves 96a to provide resistance. A second insert 58b is rotatably positioned within the second anterior cavity 44b extending from the second bridge 56 to the middle bridge 52 and away from the anterior region 36 toward the second tapered region 54b. The second insert 58b includes a second insert grooved region 94b that mate to second insert aperture grooves 96b to provide resistance. The second insert 58b includes a second insert aperture 60b extending through the second insert 58b to accept a fastener (not shown) and including a second insert taper 62b to allow the fastener (not shown) to be recessed into the second insert 58b. The second insert 58b may be secured in the second anterior cavity 44b and rotatable through the securing peg 64a, 64b, 64c, and 64d that mate to the corresponding peg aperture 98a and 98c. The first insert 58a and the second insert 58b may be smaller than the corresponding first anterior cavity 44a and second anterior cavity 44b to provide the insert gaps 88a, 88b, 88c, and 88d.

Figure 10:
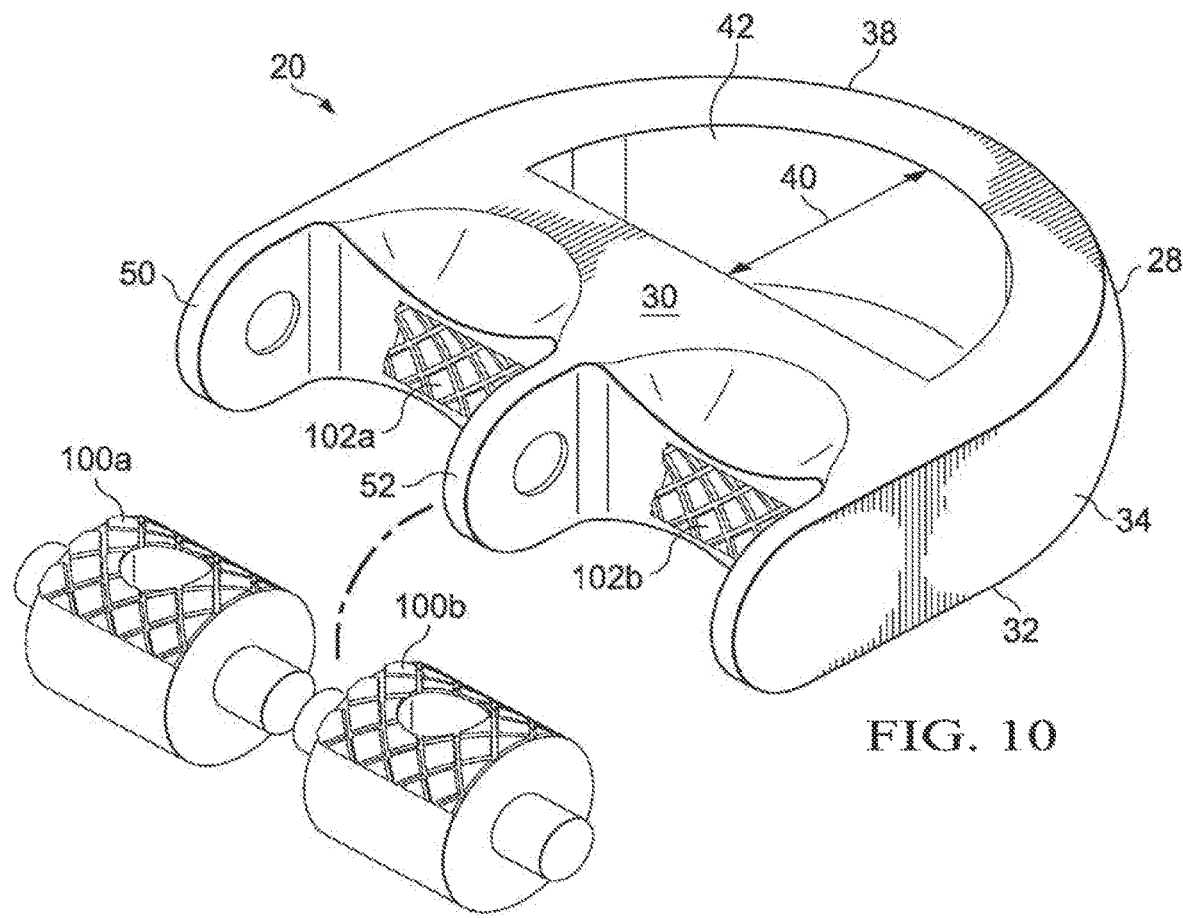
FIG. 10 is an image of another embodiment of the intervertebral disc endoprosthesis of the present invention.

FIG. 10 is an image of the intervertebral disc endoprosthesis 20 of the present invention. The disc endoprosthesis 20 includes a superior vertebral surface 30, an inferior surface 32 and a side surface 34 that extends between the superior vertebral surface 30 and inferior surface 32 to separate them. The disc endoprosthesis 20 includes an anterior region 36 that is generally flat and the posterior region 38 that is arched. Optionally, the present invention may have a recess 40 having an arched parameter 42 that extends to form the recess 40. In some embodiments, the recess 40 extends through the disc endoprosthesis 20. However, in other embodiments, the recess 40 is extended partially through the disc endoprosthesis 20 or creates an indention (not shown) into the disc endoprosthesis 20. The anterior region 36 includes a first anterior cavity 44a formed by a first cavity width 46a and a first cavity length 48a relative to the first bridge 50 and the middle bridge 52. The first anterior cavity 44*a* may include a first tapered region 54*a* extending toward the anterior region 36. The anterior region 36 also includes a second anterior cavity 44*b* formed by a second cavity width 46*b* and a second cavity length 48*b* relative to the second bridge 56 and the middle bridge 52. The second anterior cavity 44*b* may include a second tapered region 54*b* extending toward the anterior region 36. A first insert 58*a* is rotatably positioned within the first anterior cavity 44*a* extending from the first bridge 50 to the middle bridge 52 and away from the anterior region 36 toward the first tapered region 54*a*. The first insert 58*a* includes a first insert aperture 60*a* extending through the first insert 58*a* to accept a fastener (not shown) and including a first insert taper 62*a* to allow the fastener (not shown) to be recessed into the first insert 58*a*. The first insert 58*a* includes a first insert textured region 100*a* that mates to the first insert aperture textured region 102*a* to provide resistance. A second insert 58*b* is rotatably positioned within the second anterior cavity 44*b* extending from the second bridge 56 to the middle bridge 52 and away from the anterior region 36 toward the second tapered region 54*b*. The second insert 58*b* includes a second insert textured region 100*b* that mates to the second insert aperture textured region 102*b* to provide resistance. The second insert 58*b* includes a second insert aperture 60*b* extending through the second insert 58*b* to accept a fastener (not shown) and including a second insert taper 62*b* to allow the fastener (not shown) to be recessed into the second insert 58*b*. The second insert 58*b* may be secured in the second anterior cavity 44*b* and rotatable through the securing peg 64*a*, 64*b*, 64*c*, and 64*d* that mate to the corresponding peg aperture 98*a* and 98*c*. The first insert 58*a* and the second insert 58*b* may be smaller than the corresponding first anterior cavity 44*a* and second anterior cavity 44*b* to provide the insert gaps 88*a*, 88*b*, 88*c*, and 88*d*.

Figure 11:
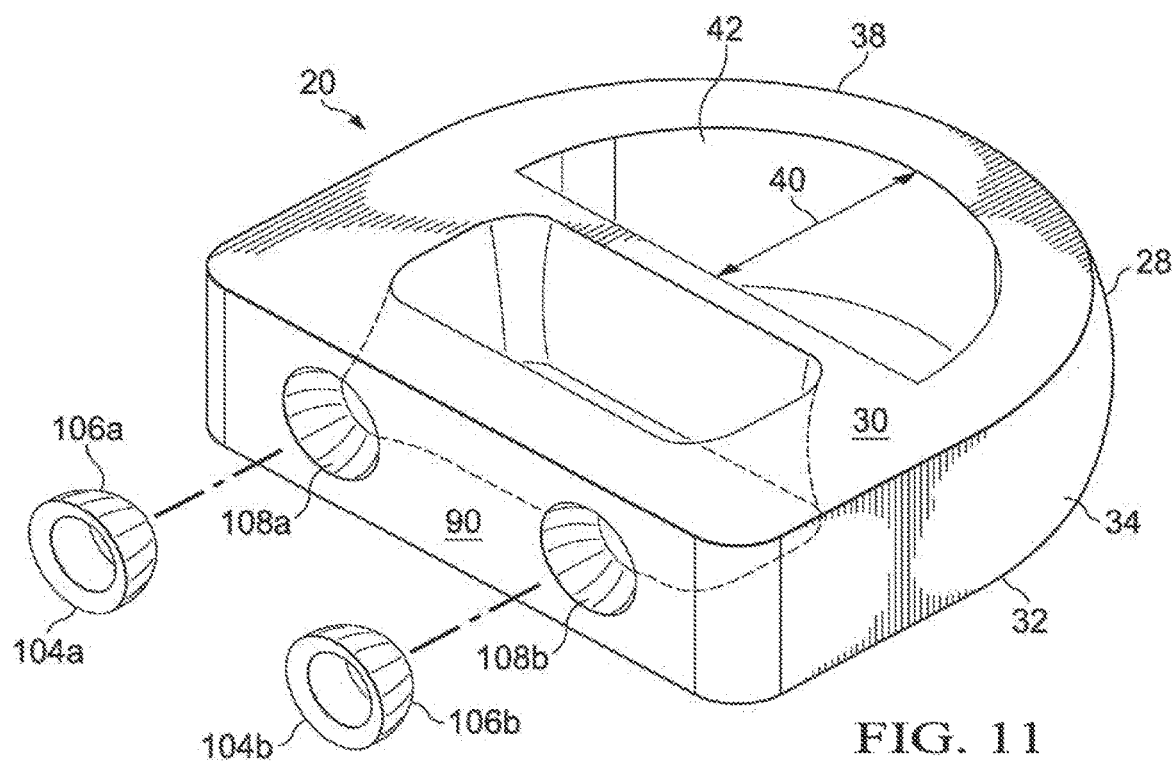
FIG. 11 is an image of another embodiment of the intervertebral disc endoprosthesis of the present invention.

FIG. 11 is an image of the intervertebral disc endoprosthesis 20 of the present invention. The disc endoprosthesis 20 includes a superior vertebral surface 30, an inferior surface 32 and a side surface 34 that extends between the superior vertebral surface 30 and inferior surface 32 to separate them. The disc endoprosthesis 20 includes an anterior region 36 that is generally flat and the posterior region 38 that is arched. Optionally, the present invention may have a recess 40 having an arched parameter 42 that extends to form the recess 40. In some embodiments, the recess 40 extends through the disc endoprosthesis 20. However, in other embodiments, the recess 40 is extends partially through the disc endoprosthesis 20 or creates an indention (not shown) into the disc endoprosthesis 20. The anterior region 36 includes an anterior surface 90 and a first anterior cavity 44 formed by a first cavity width 46 and a first cavity length 48. The first anterior cavity 44 may include a first tapered region 92 extending toward the anterior region 36. The anterior surface 90 includes a first insert aperture 60*a* having a first insert taper 62*a* and a second insert aperture 60*b* with a second insert taper 62*b* to accept a first insert jacket 104*a* with first jacket textured region 106*a* to fit into first insert aperture 60*a* with first textured region 108*a* and a second insert jacket 104*b* with second jacket textured region 106*b* to fit into the second insert aperture 60*b* having the second textured region 108*b*.

Figure 12:
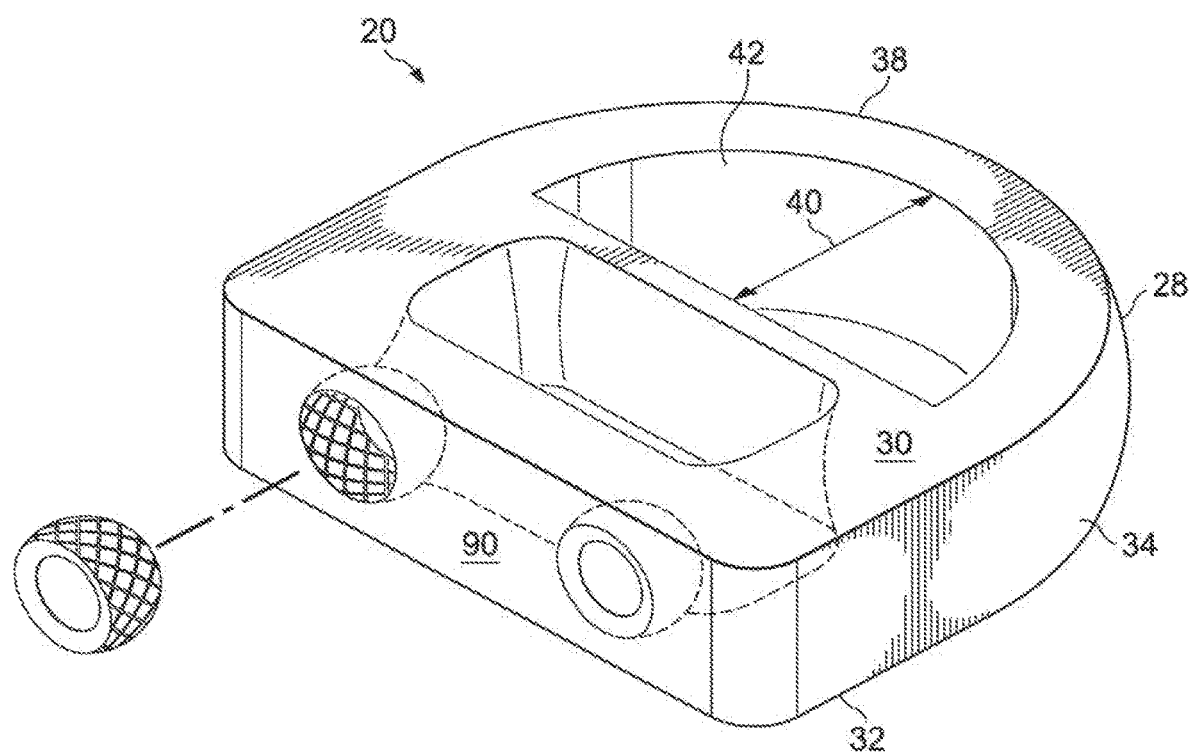
FIG. 12 is an image of another embodiment of the intervertebral disc endoprosthesis of the present invention.

FIG. 12 is an image of the intervertebral disc endoprosthesis 20 of the present invention. The disc endoprosthesis 20 includes a superior vertebral surface 30, an inferior surface 32 and a side surface 34 that extends between the superior vertebral surface 30 and inferior surface 32 to separate them. The disc endoprosthesis 20 includes an anterior region 36 that is generally flat and the posterior region 38 that is arched. Optionally the present invention may have a recess 40 having an arched parameter 42 that extends to form the recess 40. In some embodiments, the recess 40 extends through the disc endoprosthesis 20. However, in other embodiments, the recess 40 is extends partially through the disc endoprosthesis 20 or creates an indention (not shown) into the disc endoprosthesis 20. The anterior region 36 includes an anterior surface 90 and a first anterior cavity 44 formed by a first cavity width 46 and a first cavity length 48. The first anterior cavity 44 may include a first tapered region 92 extending toward the anterior region 36. The anterior surface 90 includes a first insert aperture 60*a* including a first insert taper 62*a* and a second insert aperture 60*b* with a second insert taper 62*b* to accept a first insert jacket 104*a* with first jacket textured region 106*a* to fit into first insert aperture 60*a* with first textured region 108*a* and a second insert jacket 104*b* with second jacket textured region 106*b* to fit into the second insert aperture 60*b* having the second textured region 108*b*.

Figure 13:
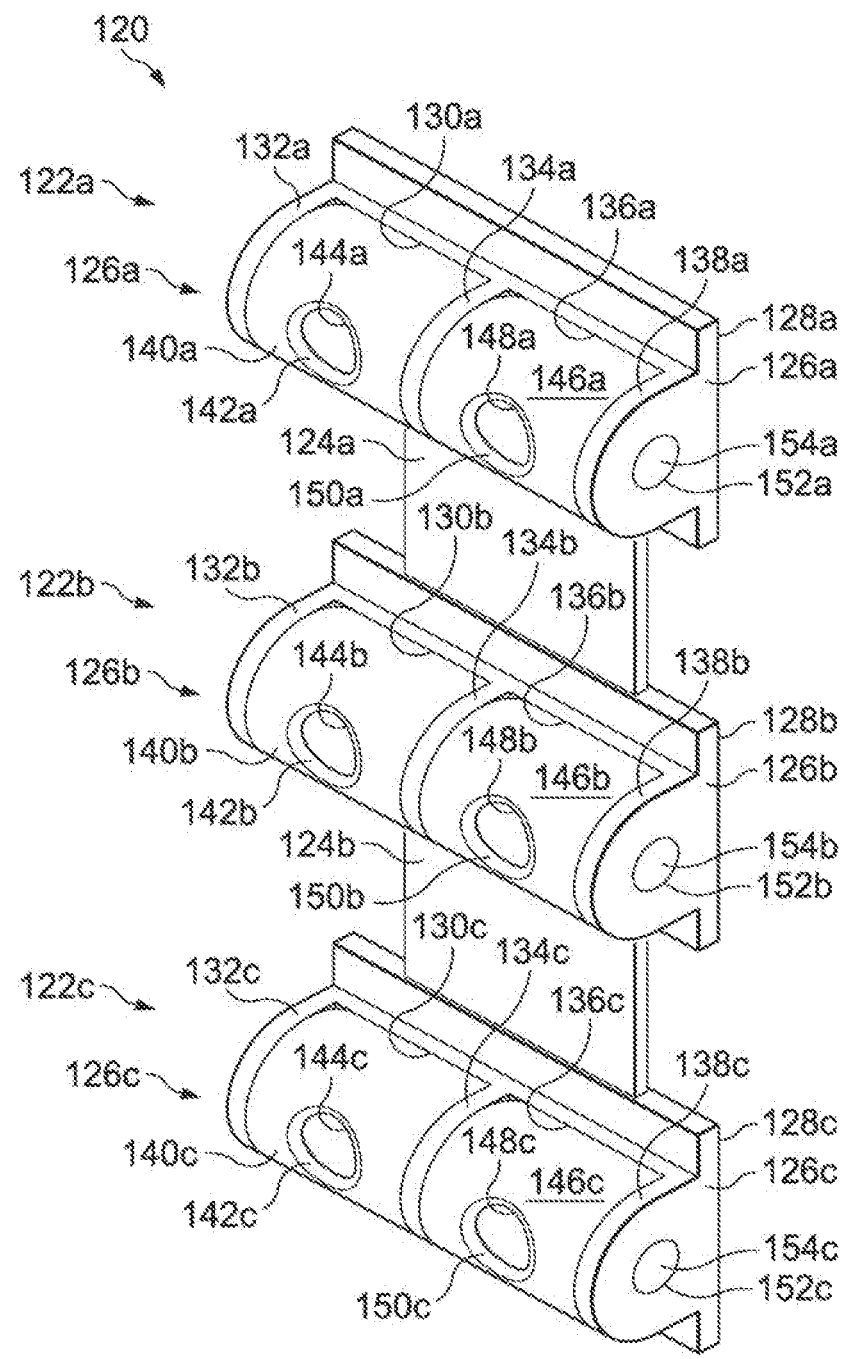
FIG. 13 is an image of the vertebral prosthesis of the present invention.

FIG. 13 is an image of the vertebral prosthesis 120 of the present invention. The vertebral prosthesis 120 includes 3 attachment fixtures 122*a*, 122*b* and 122*c* connected by connecting members 124*a* and 124*b*. The attachment fixture 122*a* includes a vertebral contacting surface 126*a* to attach to a vertebral surface (not shown). The attachment fixture 122*a* includes an anterior region 126*a* and the posterior region 128*a* that is also generally flat. The anterior region 126*a* includes a first anterior cavity 130*a* between a first bridge 138*a* and the middle bridge 134*a*. A first insert 140*a* is rotatably positioned within the first anterior cavity 130*a* extending from the first bridge 132*a* to the middle bridge 134*a*. The first insert 140*a* includes a first insert aperture 142*a* extending through the first insert 140*a* to accept a fastener (not shown) and including a first insert taper 144*a* to allow the fastener (not shown) to be recessed into the first insert 140*a*. A second insert 146*a* is rotatably positioned within the second anterior cavity 136*a* extending from the second bridge 138*a* to the middle bridge 134*a*. The second insert 146*a* includes a second insert aperture 148*a* extending through the second insert 146*a* to accept a fastener (not shown) and including a second insert taper 150*a* to allow the fastener (not shown) to be recessed into the second insert 146*a*. The second insert 146*a* may be secured in the second anterior cavity 136*a* and rotatable through the mating of a securing peg 152*a* and a securing aperture 154*a*. The attachment fixture 122*b* includes a vertebral contacting surface 126*b* to attach to a vertebral surface (not shown). The attachment fixture 122*b* includes an anterior region 126*b* and the posterior region 128*b*, that is also generally flat. The anterior region 126*b* includes a first anterior cavity 130*b* between a first bridge 138*b* and the middle bridge 134*b*. A first insert 140*b* is rotatably positioned within the first anterior cavity 130*b* extending from the first bridge 132*b* to the middle bridge 134*b*. The first insert 140*b* includes a first insert aperture 142*b* extending through the first insert 140*b* to accept a fastener (not shown) and including a first insert taper 144*b* to allow the fastener (not shown) to be recessed into the first insert 140*b*. A second insert 146*b* is rotatably positioned within the second anterior cavity 136*b* extending from the second bridge 138*b* to the middle bridge 134*b*. The second insert 146*b* includes a second insert aperture 148*b* extending through the second insert 146*b* to accept a fastener (not shown) and including a second insert taper 150*b* to allow the fastener (not shown) to be recessed into the second insert 146*b*. The second insert 146*b* may be secured in the second anterior cavity 136*b* and rotatable through the mating of a securing peg 152*b* and a securing aperture 154*b*.

The attachment fixture 122c includes a vertebral contacting surface 126c to attach to a vertebral surface (not shown). The attachment fixture 122c includes an anterior region 126c and the posterior region 128c that is also generally flat. The anterior region 126c includes a first anterior cavity 130c between a first bridge 138c and the middle bridge 134c. A first insert 140c is rotatably positioned within the first anterior cavity 130c extending from the first bridge 132c to the middle bridge 134c. The first insert 140c includes a first insert aperture 142c extending through the first insert 140c to accept a fastener (not shown) and including a first insert taper 144c to allow the fastener (not shown) to be recessed into the first insert 140c. A second insert 146c is rotatably positioned within the second anterior cavity 136c extending from the second bridge 138c to the middle bridge 134c. The second insert 146c includes a second insert aperture 148c extending through the second insert 146c to accept a fastener (not shown) and including a second insert taper 150c to allow the fastener (not shown) to be recessed into the second insert 146c. The second insert 146c may be secured in the second anterior cavity 136c and rotatable through the mating of a securing peg 152c and a securing aperture 154c.

Figure 14:
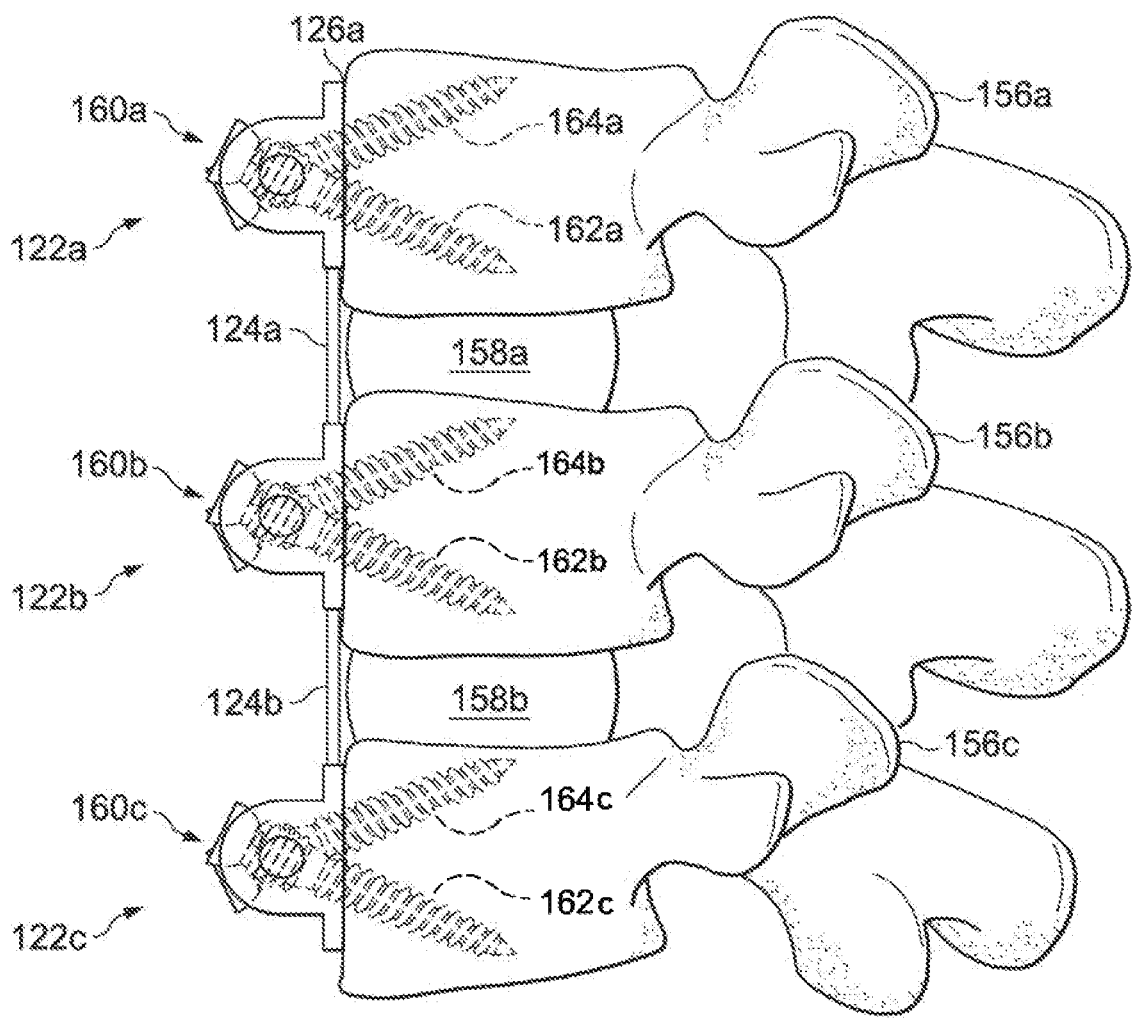
FIG. 14 is a side view of the vertebral prosthesis of the present invention in operation.

FIG. 14 is an image of the vertebral prosthesis 120 of the present invention in operation. The vertebral prosthesis 120 includes 3 attachment fixtures 122a, 122b and 122c connected by a connecting members 124a and 124b and attached to 3 vertebras 156a, 156b and 156c. The attachment fixture 122a, 122b and 122c includes a vertebral contacting surface 126a, 126b and 126c to attach to a vertebral surface. The attachment fixtures 122a, 122b and 122c are attached to the vertebra 156a, 156b and 156c with the connecting members 124a and 124b spanning the gaps occupied by disks 158a and 158b.

The attachment fixtures 122a includes an anterior region 160a with a first insert (not shown) rotatably positioned within the first anterior cavity (not shown) extending from the first bridge (not shown) to the middle bridge (not shown). The first insert (not shown) includes a first insert aperture (not shown) extending through the first insert (not shown) to accept fastener 162a. A second insert (not shown) is rotatably positioned within the second anterior cavity (not shown) extending from the second bridge (not shown) to the middle bridge (not shown). The second insert (not shown) includes a second insert aperture (not shown) extending through the second insert (not shown) to accept a fastener 164a. The second insert (not shown) may be secured in the second anterior cavity (not shown) and rotatable through the mating of a securing peg (not shown) and a securing aperture (not shown).

The attachment fixture 122b includes an anterior region 160b with a first insert (not shown) is rotatably positioned within the first anterior cavity (not shown) extending from the first bridge (not shown) to the middle bridge (not shown). The first insert (not shown) includes a first insert aperture (not shown) extending through the first insert (not shown) to accept fastener 162b. A second insert (not shown) is rotatably positioned within the second anterior cavity (not shown) extending from the second bridge (not shown) to the middle bridge (not shown). The second insert (not shown) includes a second insert aperture (not shown) extending through the second insert (not shown) to accept a fastener 164b. The second insert (not shown) may be secured in the second anterior cavity (not shown) and rotatable through the mating of a securing peg (not shown) and a securing aperture (not shown).

The attachment fixture 122c includes an anterior region 160c with a first insert (not shown) is rotatably positioned within the first anterior cavity (not shown) extending from the first bridge (not shown) to the middle bridge (not shown). The first insert (not shown) includes a first insert aperture (not shown) extending through the first insert (not shown) to accept fastener 162c. A second insert (not shown) is rotatably positioned within the second anterior cavity (not shown) extending from the second bridge (not shown) to the middle bridge (not shown). The second insert (not shown) includes a second insert aperture (not shown) extending through the second insert (not shown) to accept a fastener 164c. The second insert (not shown) may be secured in the second anterior cavity (not shown) and rotatable through the mating of a securing peg (not shown) and a securing aperture (not shown).

Figure 15:
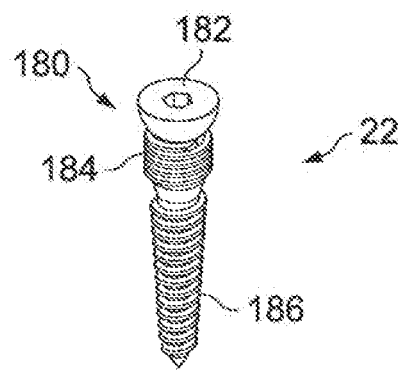
FIG. 15 is an image of a screw used in the present invention.

FIG. 15 is an image of a screw used in the present invention. The fasteners 22 may be any type of fastener that the skilled artisan may use to secure to a bone and include various thread patterns and spacings. In addition, the fastener may be constructed from materials known to the skilled artisan and used in the field and include coatings to promote growth of bone and/or reduce infection (e.g., HA coating). In one embodiment, the fastener 22 is a screw 180 that includes a screw head 182 used to fit and secure the fastener 22 to the attachment fixture (not shown). The screw head 182 is sized and shaped to contact the aperture of the attachment fixture (not shown). In communication, with the screw head 182 is a first set of threads 184 that are designed to mate to the attachment fixture (not shown) threads to secure the fastener 22 to the attachment fixture (not shown) and contact of the screw head 182 to the attachment fixture (not shown). The first set of threads 184 are in communication with a second set of threads 186 that are designed to penetrate bone and secure the fastener 22 to the bone. The screw head 182 is designed to be larger than the aperture in the attachment fixture (not shown) so as not to pass through the attachment fixture (not shown) but secure the fastener 22 to the attachment fixture (not shown). The first set of threads 184 are designed to be smaller than the screw head 182 and designed to mate to the threads of the aperture in the attachment fixture (not shown) to secure the fastener 22 to the attachment fixture (not shown). The second set of threads 186 are designed to be smaller than the aperture in the attachment fixture (not shown) so as to pass through the attachment fixture (not shown) into the bone (not shown).

The attachment fixture may be of a size slightly larger or smaller as necessary to accommodate the size of the individual. The present invention may be made in part or whole from materials or combinations of materials that provide sufficient strength and flexibility, while remaining bio-compatible, e.g., metals, nonmetals, rubbers, plastics, vinyls, polymers, composites, non-reinforced biocompatible polymers, two-phase biocompatible polymers, plastics reinforced with dissimilar polymers, filaments and combinations thereof.

In addition the device of the present invention may be positioned between the vertebrae at different positions as necessary given the specific application. This positioning is accomplished by the ability of the insert to rotate. This rotation allows the angle of the screw to be varied as needed to position the insert between the vertebrae. For example, insert may be positioned deeply between the vertebrae and the rotation allows the screws to be inserted into the vertebrae without protruding or damaging the vertebrae.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for stabilizing vertebral bodies, said method comprising:
    providing a vertebral implant including:
        a first attachment fixture having a first anterior region and a first posterior region;
        a first insert having a first fastener aperture and disposed within a first anterior cavity of the first anterior region, wherein the first insert is rotatable in the first anterior cavity;
        a second insert having a second fastener aperture and disposed within a second anterior cavity of the first anterior region, wherein the second insert is rotatable in the second anterior cavity;
        a second attachment fixture having a second anterior region and a second posterior region;
        a third insert having a third fastener aperture and disposed within a third anterior cavity of the second anterior region, wherein the third insert is rotatable in the third anterior cavity;
        a fourth insert having a fourth fastener aperture and disposed within a fourth anterior cavity of the second anterior region, wherein the fourth insert is rotatable in the fourth anterior cavity;
        a third attachment fixture having a third anterior region and a third posterior region;
        a fifth insert having a fifth fastener aperture and disposed within a fifth anterior cavity of the third anterior region, wherein the fifth insert is rotatable in the fifth anterior cavity;
        a sixth insert having a sixth fastener aperture and disposed within a sixth anterior cavity of the third anterior region, wherein the sixth insert is rotatable in the sixth anterior cavity;
    fixating the first attachment fixture to a first vertebral body;
    fixating the second attachment fixture to a second vertebral body;
    fixating the third attachment fixture to a third vertebral body;
    coupling, via a first connecting member, the first attachment fixture to the second attachment fixture; and
    coupling, via a second connecting member, the second attachment fixture to the third attachment fixture
    wherein the vertebral implant has a first fastener including:
        a head sized and shaped to contact the first fastener aperture of the first insert; and
        a first set of proximal threads adapted to mate with complimentary threads of the first fastener aperture of the first insert, and
    wherein each of the first insert, second insert, third insert, fourth insert, fifth insert, and sixth insert are cylinders each having two bases separated by a curved outer surface extending around the two bases, and wherein each of the first fastener aperture, second fastener aperture, third fastener aperture, fourth fastener aperture, fifth fastener aperture, and sixth fastener aperture is disposed on the curved outer surface of a respective one of the first insert, second insert, third insert, fourth insert, fifth insert, and sixth insert.

2. The method of claim 1, wherein the first insert is rotatable independent of the second insert, wherein the third insert is rotatable independent of the fourth insert, and wherein the fifth insert is rotatable independent of the sixth insert.

3. The method of claim 1, wherein the first insert comprises a first tapered region tapering toward the first anterior cavity, the second insert comprises a second tapered region tapering toward the second anterior cavity, the third insert comprises a third tapered region tapering toward the third anterior cavity, the fourth insert comprises a fourth tapered region tapering toward the fourth anterior cavity, the fifth insert comprises a fifth tapered region tapering toward the fifth anterior cavity, and the sixth insert comprises a sixth tapered region tapering toward the sixth anterior cavity.

4. The method of claim 1, wherein each attachment fixture includes a vertebral contacting surface configured to be attached to a vertebral surface.

5. The method of claim 1, wherein the first, second, and third posterior regions are generally flat.

6. The method of claim 1, wherein the first anterior cavity is defined by a first bridge and a first middle bridge and the second anterior cavity is defined by the first middle bridge and a second bridge, wherein the third anterior cavity is defined by a third bridge and a second middle bridge and the fourth anterior cavity is defined by the second middle bridge and a fourth bridge, and wherein the fifth anterior cavity is defined by a fifth bridge and a third middle bridge and the sixth anterior cavity is defined by the third middle bridge and a sixth bridge.

7. The method of claim 6, wherein each of the first, second, third, fourth, fifth, and sixth inserts is secured in its respective anterior cavity by a respective pair of securing pegs extending into corresponding respective pairs of securing apertures formed in the pair of bridges that define the respective anterior cavity.

8. The method of claim 1, wherein the first fastener further includes a second set of distal threads adapted to penetrate a bone.

9. A method for stabilizing vertebral bodies, said method comprising:
   providing a vertebral implant including:
      a first attachment fixture having a first anterior region and a first posterior region;
      a first insert having a first fastener aperture and disposed within a first anterior cavity of the first anterior region, wherein the first insert is rotatable in the first anterior cavity;
      a second insert having a second fastener aperture and disposed within a second anterior cavity of the first anterior region, wherein the second insert is rotatable in the second anterior cavity;
      a second attachment fixture having a second anterior region and a second posterior region;
      a third insert having a third fastener aperture and disposed within a third anterior cavity of the second anterior region, wherein the third insert is rotatable in the third anterior cavity;
      a fourth insert having a fourth fastener aperture and disposed within a fourth anterior cavity of the second anterior region, wherein the fourth insert is rotatable in the fourth anterior cavity;
      a third attachment fixture having a third anterior region and a third posterior region;
      a fifth insert having a fifth fastener aperture and disposed within a fifth anterior cavity of the third anterior region, wherein the fifth insert is rotatable in the fifth anterior cavity;
      a sixth insert having a sixth fastener aperture and disposed within a sixth anterior cavity of the third anterior region, wherein the sixth insert is rotatable in the sixth anterior cavity;
   coupling, via a first connecting member, the first attachment fixture to the second attachment fixture; and
   coupling, via a second connecting member, the second attachment fixture to the third attachment fixture,
   wherein the vertebral implant has a first fastener including:
      a head sized and shaped to contact the first fastener aperture of the first insert; and
      a first set of proximal threads adapted to mate with complimentary threads of the first fastener aperture of the first insert, and
   wherein each of the first insert, second insert, third insert, fourth insert, fifth insert, and sixth insert are cylinders each having two bases separated by a curved outer surface extending around the two bases, and wherein each of the first fastener aperture, second fastener aperture, third fastener aperture, fourth fastener aperture, fifth fastener aperture, and sixth fastener aperture is disposed on the curved outer surface of a respective one of the first insert, second insert, third insert, fourth insert, fifth insert, and sixth insert.

10. The method of claim 9, wherein the first insert is rotatable independent of the second insert, wherein the third insert is rotatable independent of the fourth insert, and wherein the fifth insert is rotatable independent of the sixth insert.

11. The method of claim 9, wherein the first insert comprises a first tapered region tapering toward the first anterior cavity, the second insert comprises a second tapered region tapering toward the second anterior cavity, the third insert comprises a third tapered region tapering toward the third anterior cavity, the fourth insert comprises a fourth tapered region tapering toward the fourth anterior cavity, the fifth insert comprises a fifth tapered region tapering toward the fifth anterior cavity, and the sixth insert comprises a sixth tapered region tapering toward the sixth anterior cavity.

12. The method of claim 9, wherein each attachment fixture includes a vertebral contacting surface configured to be attached to a vertebral surface.

13. The method of claim 9, wherein the first, second, and third posterior regions are generally flat.

14. The method of claim 9, wherein the first anterior cavity is defined by a first bridge and a first middle bridge and the second anterior cavity is defined by the first middle bridge and a second bridge, wherein the third anterior cavity is defined by a third bridge and a second middle bridge and the fourth anterior cavity is defined by the second middle bridge and a fourth bridge, and wherein the fifth anterior cavity is defined by a fifth bridge and a third middle bridge and the sixth anterior cavity is defined by the third middle bridge and a sixth bridge.

15. The method of claim 14, wherein each of the first, second, third, fourth, fifth, and sixth inserts is secured in its respective anterior cavity by a respective pair of securing pegs extending into corresponding respective pairs of securing apertures formed in the pair of bridges that define the respective anterior cavity.

16. The method of claim 9, wherein the first fastener further includes a second set of distal threads adapted to penetrate a bone.

* * * * *